United States Patent [19]

D'Orazio

[11] 4,144,318

[45] Mar. 13, 1979

[54] MOSQUITO COIL COMPOSITION AND PROCESS FOR MAKING THE SAME

[75] Inventor: Vincent T. D'Orazio, Racine, Wis.

[73] Assignee: S. C. Johnson & Son, Inc., Racine, Wis.

[21] Appl. No.: 822,108

[22] Filed: Aug. 5, 1977

[51] Int. Cl.² ............................................. A01N 17/04
[52] U.S. Cl. ....................................... 424/40; 424/42; 424/186; 424/285; 424/306
[58] Field of Search ................... 424/40, 42, 306, 196, 424/285

[56] References Cited

U.S. PATENT DOCUMENTS 3,723,615  3/1973  Okuno ..................................... 424/40

FOREIGN PATENT DOCUMENTS 4816615  7/1969  Japan.
4628120  9/1969  Japan.

Primary Examiner—V. D. Turner

[57] ABSTRACT

An improved mosquito coil composition comprising from 72–83% by weight based on dry ingredients of a carrier selected from sawdust having a particle size between 70 and 200 mesh, coconut shell flour, pyrethrum marc, and mixtures thereof, from 16–26% by weight based on dry ingredients potato starch and 0.5–3% by weight based on dry ingredients of an insecticide. The process comprises dispersing the starch in water heated to a temperature of from 40°–65° C., adding water having a temperature of between 80°–95° C. to the dispersed water-starch mixture, mixing the starch-water gel with the filler and insecticide, extruding the mixture into a ribbon, forming the mosquito coils from this ribbon, and drying the formed mosquito coils.

2 Claims, No Drawings

MOSQUITO COIL COMPOSITION AND PROCESS FOR MAKING THE SAME

BACKGROUND OF THE INVENTION

This invention relates to an improved mosquito coil composition and process for making this improved mosquito coil. More particularly, this invention relates to an improved mosquito coil composition utilizing potato starch as a binder for the mosquito coil.

The manufacture of mosquito coils is an art which has been practiced for a number of years. Mosquito coils comprise a material which burns emitting smoke combined with an insecticide. Mosquito coils are often used to knock down or repel flying insects in living quarters.

Traditional mosquito coil compositions include approximately 25% or more of a residue from preparing pyrethrum known as pyrethrum marc, as it is thought this material is a necessary ingredient to produce an acceptable mosquito coil. In addition to the pyrethrum marc, the prime burning agent or fuel used for mosquito coils is coconut shell flour, tabu powder, sawdust, ground leaves, ground bark, starch, etc.

Representative patents describing mosquito coils are U.S. Pat. Nos. 3,248,287, 3,723,615 and 3,819,823. The latter two patents are primarily directed to insecticides for use in mosquito coils and describe the use of various mosquito coil carrier ingredients such as wood powder and starch.

It has unexpectedly been found that a high quality mosquito coil composition can be prepared by utilizing from 16-25% by weight based on dry ingredients of potato starch as the binder for the traditional mosquito coil carrier material. It has also been found that these improved mosquito coils may be prepared by a method which involves dispersing the potato starch in water which has a temperature just below the gellation point of the potato starch, adding sufficient hot water to this water-starch mixture to raise the temperature above the gellation point of the potato starch, adding the dry ingredients to the mosquito coil, extruding the coil into a ribbon, stamping the mosquito coils from this ribbon, and allowing these coils to dry.

The coils prepared using the composition of the present invention and the method of the present invention have good burning properties lasting up to 7 or 8 hours and have better structural integrity than coils made using other starches.

It is, therefore, the primary object of the present invention to prepare a mosquito coil composition utilizing potato starch as a binding agent.

It is a further object of the present invention to provide a mosquito coil composition having improved burning properties and structural integrity.

It is a still further object of the present invention to provide a mosquito coil composition having controllable and even-burning properties.

It is a still further object of the present invention to provide a process for quickly and easily producing high quality mosquito coils.

Other objects and advantages of the mosquito coil composition and process for preparing the same will become more apparent from the following, more detailed description thereof.

The mosquito coil compositions of the present invention comprise on a dry weight basis from 16-26% by weight of potato starch, from 72-83% by weight of a mosquito coil carrier agent, from 0-2% of a burning aid, from 0.5-3% by weight of an insecticidal material.

The method of the present invention comprises dispersing potato starch in water heated to a temperature of 30-65° C., gelling the starch by adding sufficient water having a temperature of from 80-95° F. to the starch-water dispersion to raise the temperature of the mixture to above the gelling point of the starch, adding the mosquito coil carrier to the gelled starch-water mixture, forming the composition into a thin sheet, forming the mosquito coils from this thin sheet and drying the formed mosquito coils.

DETAILED DESCRIPTION OF THE INVENTION

All references to mesh sizes in the specification and claims are to U.S. Sieve Series mesh.

The improved mosquito coils of the present invention use potato starch as a binding agent. Although starches have been incorporated into mosquito coil compositions in the past, neither has the particular use of potato starch as such nor have the unexpected properties, i.e., ease of production, high strength, of a mosquito coil using particular percentages of potato starch been recognized in the prior art.

Although substantially any potato starch can be utilized, the starch used must be dispersable in water at a temperature below the gellation point of the potato starch, about 66.5° C. On a dry basis of the mosquito coil, the coil must contain from 16-26% by weight of potato starch and preferably from 18-23% by weight potato starch and optimumly from 19-21% by weight potato starch. Other starches, such as corn starch, rice starch, wheat starch, etc., cannot be substituted for the potato starch in the coil of the present invention, although small percentages which do not effect the performance may be present, as long as the potato starch content is within the above ranges. When the starches, other than potato starch, are used as the sole binding agent, the mosquito coils produced are inferior as compared to the mosquito coil of the present invention.

Only potato starch can be utilized in the method of the present invention since the gellation temperature of most other starches is too high, i.e., about 90-95° C., to permit the mixture of starch-water to be raised and maintained above the gellation temperature for sufficient time to properly gel the starch. However, even when these other starches are gelled properly by cooking, the resulting coils have lower structural integrity.

Structural integrity of the formed mosquito coil is quite important as the coil must be sufficiently strong so as not to break on packaging, shipping and use. A broken coil is of little value as the burning time of the fragments is greatly reduced.

The mosquito coils of the present invention do include a substantial percentage of the dry basis of the coil of conventional mosquito coil carrier ingredients, generally from 72-83% by weight and preferably from 74-80% by weight and optionally from 75-78% by weight. Representative ingredients include pyrethrum marc, coconut shell flour, sawdust having a particle size from 70-200 mesh, tabu powder, and mixtures thereof. Although substantially any combination of conventional carrier ingredients can be utilized in mosquito coils of the present invention, it is preferred to utilize hardwood sawdust having a particle size between about 70-200 mesh and particularly between 100-200 mesh. By utilizing the sawdust having this particle size, the burning rate of the mosquito coils can be accurately controlled and can provide mosquito coils which burn up to 7 to 8 hours.

As a primary purpose of the mosquito coils of the present invention is to repel, knock down and/or kill flying insects which may be present in living quarters, the mosquito coil should have an effective amount of an insecticide or repellant. Generally, this is from 0.5–3% by weight of an insecticidal agent or repellent. Traditionally, pyrethrum or pyrethroid type materials have been utilized in mosquito coil compositions. Substantially any pyrethroid can be utilized and incorporated into the mosquito coil of the present invention. Preferred pyrethroids from the standpoint of expense and activity are pyrethrum, resmethrin, bioallethrin, allethrin, and mixtures thereof. The particularly preferred insecticide for use in the mosquito coils of the present invention is an emulsifiable concentrate of allethrin.

The mosquito coils of the present invention also incorporate various burning aids which aid in sustaining the burning of the mosquito coil throughout the life of the same. Traditional and conventional burning aids can be utilized, such as sodium and potassium nitrate, sodium benzoate, and mixtures thereof. Generally, these burning aids are present in the composition from 0–2% and preferably from 0.3–0.75% by weight on the dry basis.

Other ingredients may be incorporated into the mosquito coil, such as dyes, pigments, etc., to improve the aesthetic properties of the same.

Lastly, during the manufacture of mosquito coils in accordance with the method of the present application, it is necessary to incorporate substantial quantities of water to gel the starch and to enable the dry ingredients to be completely and intimately mixed. Generally, it is preferred that, for appropriate and ease of handling, the dry ingredients are mixed in a ratio of dry ingredients to water of from about 1:1 to about 1:2.5. Excess water is to be avoided as the water must be removed during the drying step.

The method of the present invention comprises mixing the starch with sufficient water heated to a temperature of between 40–65° C. to disperse the starch. After the starch is well dispersed into this mixture, sufficient water heated to a temperature in the range of 80–95° C. is added to gel the starch by raising the temperature above the gellation point of the starch. Subsequent to the gellation of the starch, the carrier material, such as sawdust, is then added to the gelled starch-water mixture to form a putty-like mass which is extruded into a ribbon or sheet from which the mosquito coils are formed by stamping or other conventional method. After the mosquito coils are formed, they are then dried by any conventional means, such as forced air drying in an oven.

Depending on the particular insecticidal material, dyes, and burning aids used, these materials may be incorporated into the composition as a water dispersion in the initial starch-dispersion or as dry ingredients with the carriers. For ease of processing and uniformity of dispersion throughout the coil, it is preferred to use water dispersible insecticides, dyes and burning aids which are added to the water used to disperse the starch.

The composition and method of the present invention will now be illustrated by way of the following examples. Unless otherwise specified, all parts and percentages are by weight and all temperatures and degrees are Celsius.

EXAMPLE 1 & COMPARATIVE EXAMPLES 1–3

Some 25 parts by weight of the starches shown in Table I were dispersed in 75 parts by weight of water heated to 60° C. by stirring, the water including 1% emulsifiable allethrin. After the starch was dispersed, 100 parts by weight water heated to 82° C. was added. Next, 75 parts by weight of sawdust having a particle size of 80 mesh were mixed to the starch gel. Only the potato starch gave a mixture suitable for extrusion into mosquito coils. A ribbon was extruded from the potato starch-sawdust mixture, stamped into coils, and oven dried.

TABLE I

|  | Ex. 1 | Comp. Ex. 1 | Comp. Ex. 2 | Comp. Ex. 3 |
|---|---|---|---|---|
| Sawdust | 75 | 75 | 75 | 75 |
| Potato Starch | 25 | — | — | — |
| Rice Starch | — | 25 | — | — |
| Corn Starch | — | — | 25 | — |
| Wheat Starch | — | — | — | 25 |
| Water | 175 | 175 | 175 | 175 |

As the temperature of the mixture for Comparative Examples 1–3 was below the gellation temperature of the starches used, the water-starch dispersions were cooked for 30 minutes at a temperature above the gelling points of the starch. This gelled material was mixed with the sawdust, dried, and stamped into coils. When these coils were compared to the coils of Example 1 by dropping the coils and pulling on the coils, more of the coils of Comparative Examples 1–3 broke than those of Example 1.

EXAMPLES 2–8

A series of mosquito coils was made using the process of Example 1, varying the type of sawdust, the amount of sawdust and the amount of potato starch, as shown in Table II.

TABLE II

| Example # | Sawdust Size (Mesh) | Sawdust % Dry Basis | Starch % Dry Basis |
|---|---|---|---|
| 2 | 70 | 74 | 25 |
| 3 | 80 | 75 | 24 |
| 4 | 100 | 76 | 23 |
| 5 | 10 parts 200/90 parts 100 | 78 | 21 |
| 6 | 20 parts 200/80 parts 100 | 78.5 | 20.5 |
| 7 | 30 parts 200/70 parts 100 | 79 | 20 |
| 8 | 50 parts 200/50 parts 100 | 80 | 19 |

Each of the mixes could be extruded to form an acceptable coil. As is apparent from the above table, the courser the filler, sawdust, the more starch is required.

EXAMPLE 9

The mosquito coil of Example 1 is prepared except the following insecticides are substituted for the allethrin:

A—Bioallethrin
B—Pyrethrum extract
C—Resmethrin

Each of the above produced an acceptable mosquito coil.

What I claim is:
1. A process for preparing mosquito coils comprising:

(a) Dispersing from 16–26% by weight on a dry basis potato starch in water having a temperature of from 40–60° C.;
(b) Gelling the dispersed starch by adding sufficient water having a temperature of from 80–95° C. to the starch-water dispersion to raise the temperature of the resulting mixture to above the gelling point of the starch;
(c) Adding from 72–83% by weight on a dry basis of a carrier, from 0.5—3% by weight on a dry basis of an insecticide and from 0–2% by weight on a dry basis of a burning aid to the gelled starch-water mixture;
(d) Forming thin sheets from the carrier starch-water mixture;
(e) Forming mosquito coils from the thin sheets; and
(f) Drying the formed mosquito coils with the proviso that the ratio of dry ingredients to water is within the range of from 1:1–1:2.5.

2. A process for preparing mosquito coils comprising:
(a) dispersing from 16–26% by weight on a dry basis potato starch in water having a temperature of from 40–65° C., the water containing 0.5–3% by weight on a dry basis of an insecticide and 0–2% by weight on a dry basis of a burning aid;
(b) gelling the dispersed starch by adding sufficient water having a temperature of from 80–95° C. to the starch-water dispersion to raise the temperature of the resulting mixture to above the gelling point of the starch;
(c) adding from 72–83% by weight on a dry basis of a carrier to the gelled starch-water mixture;
(d) forming thin sheets from the carrier - starch-water mixture;
(e) forming mosquito coils from the thin sheets; and
(f) drying the formed mosquito coils, with the proviso that the ratio of dry ingredients to water is within the range of 1:1 to 1:2.5.

* * * * *